United States Patent [19]

Jacobs

[11] 4,453,941
[45] Jun. 12, 1984

[54] COMPOSITION AND PROCESS FOR PRODUCING PIGMENTATION IN HAIR OR SKIN

[75] Inventor: Merle E. Jacobs, Goshen, Ind.

[73] Assignee: Board of Overseers of Goshen College, Goshen, Ind.

[21] Appl. No.: 439,802

[22] Filed: Nov. 8, 1982

Related U.S. Application Data

[62] Division of Ser. No. 220,449, Dec. 29, 1980, Pat. No. 4,390,341.

[51] Int. Cl.³ .................. A61K 7/13; A61K 7/42; A61K 7/44; A61K 7/021
[52] U.S. Cl. .................................. 8/424; 8/405; 8/406; 8/429; 424/59; 424/60; 424/63
[58] Field of Search ............... 8/405, 406, 424, 429, 8/436; 424/59, 60, 63

[56] References Cited

U.S. PATENT DOCUMENTS 3,970,423 7/1976 Brody et al. ................. 8/10.2
4,021,538 5/1977 Yu et al. ....................... 424/60
4,145,413 3/1979 Usdin et al. ................... 424/63

FOREIGN PATENT DOCUMENTS 2932923 2/1981 Fed. Rep. of Germany ........ 424/59
54-110337 8/1979 Japan .............................. 8/405
744438 2/1956 United Kingdom ............... 8/405

OTHER PUBLICATIONS

*Chemical and Physical Behavior of Human Hair*, by Clarence R. Robbins, published by Van Nostrand Reinhold Company, pp. 67–79 and 113–132, (1979).
Cataractogenous Effect of Hair Dyes: A Clinical and Experimental Study, by I. S. Jain et al., *Annals of Ophthalmology*, pp. 1681–1686, (Nov. 1979).
Products of In Vitro Oxidation of N-Acetyldopamine as Possible Components in the Sclerotization of Insect Cuticle, by Martin G. Peter, *Insect Biochem.*, vol. 10, pp. 221–227, (1980).
Influence of Beta-Alanane on Ultrastructure Tanning and Melanization of *Drosophila Melanogaster* Cuticles, by M. E. Jacobs, *Biochemical Genetics*, vol. 18, Nos. 1/2, pp. 65–76, (1980).
N-Acetyldopamine as Sclerotizing Agent of the Insect Cuticle, by Peter Karlson et al., *Nature*, vol. 195, pp. 183–184, (Jul. 14, 1962).
Beta-Alanine and Cuticle Maturation in Drosophila, by Ross Hodgetts et al., *Nature*, vol. 252, pp. 710–711, (Dec. 20/27, 1974).
Studies on the Incorporation of Beta-Alanine into the Puparium of the Fly, *Sarcophaga Bullata*, by R. P. Bodnaryk, *J. Insect Physiol.*, vol. 17, pp. 1201–1210, (1971).
An Enzyme from Locust Cuticle Involved in the Formation of Crosslinks from N-Acetyldopamine, by S. O. Andersen, *J. Insect Physiol.*, vol. 18, pp. 527–540, (1972).
On the Metabolism of N-Acetyldopamine in *Periplaneta Americana*, by Robert P. Bodnaryk et al., *J. Insect Physiol.*, vol. 20, pp. 911–923, (1974).

*Primary Examiner*—Albert T. Meyers
*Assistant Examiner*—John M. Kilcoyne
*Attorney, Agent, or Firm*—Trexler, Bushnell & Wolters, Ltd.

[57] ABSTRACT

A composition and process for producing pigmentation in hair and skin is disclosed which employs non-mutagenic compounds to duplicate naturally occurring biosynthetic colors. The composition for imparting golden coloration comprises as active ingredients a solution of a tyrosine derivative having a side chain with a substituted amine group in admixture with certain compounds having a reactive nitrogen moiety, and is topically applied in the presence of an oxidant. The composition for imparting a dark coloration comprises as active ingredients a solution of tyrosine derivative having a side chain free for indole formation in admixture with certain compounds having a reactive nitrogen moiety, and is topically applied in the presence of an oxidant. Mixtures of the two compositions may be applied to impart proportionate intermediate colors.

14 Claims, No Drawings

COMPOSITION AND PROCESS FOR PRODUCING PIGMENTATION IN HAIR OR SKIN

This application is a division of application Ser. No. 220,449, filed Dec. 29, 1980, now U.S. Pat. No. 4,390,341.

The invention described herein was made in the course of work under a grant from the Department of Health and Human Services.

The present invention relates to a composition and process for producing natural pigments in human hair and skin to provide variations of the natural colors therein.

Heretofore, the color of hair has been modified by bleaching or by the addition of artificial colors. Hydrogen peroxide remains the primary oxidizing agent in modern bleaching compositions, with persulfate salts often added as accelerators. Such bleaching often results in an artificial blond color, lacking the russet luster which is present in natural blond hair. In addition, as the oxidative reaction required for bleaching is severe, damaging side reactions also occur which include changes in the tensile, frictional and cosmetic properties of hair. This occurs mainly because of oxidative attack on the disulfide bonds in the hair fiber.

Numerous products exist for imparting a darker coloration to human hair. Oxidative hair dyes generally consist of derivatives of aniline mixed with substituted resorcinols or meta-phenylene diamines and an oxidizing agent. Most dyes contain ingredients acting as dye precursors and several reactions are involved, each contributing to hair color. Unfortunately, most of these compounds are allergenic and have been found to be carcinogenic in mammals or mutagenic in microorganisms. Aside from these physiological problems, the harsh chemicals used in the prior art bleaching and dyeing processes often yield an unnatural color and unexpected reactions if treated subsequently with permanent waves or other hair treatments.

Therefore, it is an object of the present invention to provide a composition and related method for the production of pigmentation in hair which closely duplicates the natural shades of human hair.

It is also an object of the present invention to provide compositions for altering the coloration of hair which are not toxic, mutagenic, or otherwise harmful to the hair or the human body.

Other additional objects will be readily apparent from the following description and claims.

Melanin is known in the art as the pigment which provides the dark color in hair. Melanin has been described as either a complex random polymer largely based upon, or a homopolymer consisting of, 5,6-dihydroxyindole:

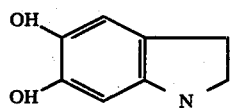

It is also known in the art that melanin may be synthesized by the oxidation of the amino acids dopa or tyrosine.

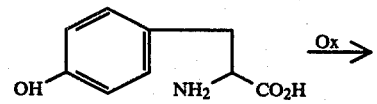

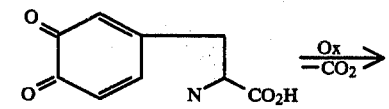

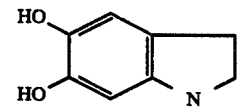

According to the present invention, the lighter colors found in human hair are believed to be produced by the presence, in the hair matrix, of varying proportions of a gold colored complex molecule. This gold colored complex, based on the amino acid tyrosine which is abundant in hair proteins, is shown by the formula:

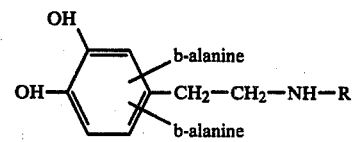

wherein R is an acetyl group, a protein, or an amino acid which serves to prevent the formulation of the indole ring found in melanin.

The basis for the gold color of blond hair is thus believed to be beta-alanine complexed with a dihydroxy tyrosyl derivative having a side chain which is not free for indolization, or a polymer thereof. It has been found that human hair may be given a blond color through the use of certain omega amino acids, such as beta-alanine, in reaction with the quinone resulting from the oxidation of N-acetyldopamine or the tyrosyl derivatives. Structurally, the reaction of beta-alanine with N-acetyldopamine is shown by the formula:

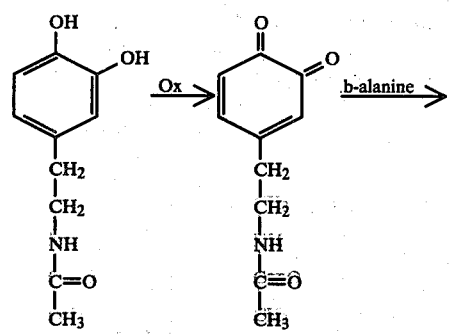

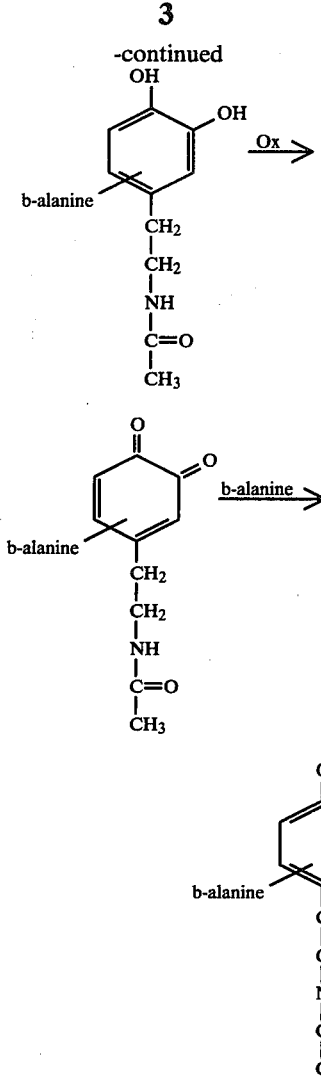

It can be seen that, in the case of N-acetyldopamine, the acetyl group prevents the formation of an indole ring by the side chain during the existence of the nascent quinone. This allows the dipolar beta-alanine to attach to the phenol ring to form the natural gold colored complex.

In a first example, lengths of gray human hair were soaked in a 0.1 M copper chloride solution. The hair was then rinsed, and soaked at 25° C. in a mixture of 0.01 M N-acetyldopamine and 0.1 M beta-alanine. The hair immediately assumed a golden blond color throughout which remained stable and resisted water extraction at 100° C.

In a second example, 0.01 M leucyl-tyrosine was substituted for N-acetyldopamine in the above-described experiment. The hair again assumed a natural blond color throughout, although the reaction rate was somewhat slower than that described for N-acetyldopamine.

The reactions of leucyl-tyrosine and N-acetyldopamine demonstrate that natural blond pigments may be produced in hair according to the above-described reactions through the use of a tyrosyl derivative having a side chain not free for indolization, for example, a side chain having a substituted amine group.

Repeated experiments were performed to determine alternatives to beta-alanine in the above-described reaction. These experiments showed that short chain aliphatic compounds, i.e. with carbon chains of up to 6 carbon atoms, which have a reactive nitrogen moiety in the beta or higher position, will produce blond pigmentation in hair when substituted for beta-alanine in the above-described reaction. Amino acids having an amino group free from carboxyl hindrance such as lysine, gamma-amino-butyric acid and b-aminoisobutyric acid all gave satisfactory results, as did b-aminopropionitrile. As opposed to these omega-amino compounds alpha-amino acids, when substituted for beta-alanine in the above-described reaction, either failed to react or gave green reaction products.

Studies have shown that the pigments induced by the process of the present invention are seemingly identical to natural pigments. High pressure liquid chromatographs of the natural blond pigment which is extractable from blond or brown hair at 100° C., show the same pattern as the extractable gold pigment resulting from the above-described reaction of beta-alanine and N-acetyldopamine. Also, the increased presence of beta-alanine in natural gold hair has been shown by the chromatographic patterns of extracted pigments which show the highest amount (0.21%) of beta-alanine in extracts of light blond hair and the lowest amount (0.12%) in extracts of black hair.

As was mentioned above, melanin is thought to be a complex aggregate of quinoid pigment in a protein matrix. So-called synthetic melanin has been obtained by the action of tyrosinase on dopa. According to a process of the present invention, it has been found that when a tyrosine derivative having an aliphatic side chain free for indole formation, in admixture with a short chain aliphatic compound containing a reactive nitrogen moiety in the beta or higher position, is applied to hair in the presence of an oxidant such as copper chloride, a rich, dark color is produced. The addition of the omega nitrogen compound, such as beta-alanine, greatly enhances the known oxidation of a tyrosine derivative to synthetic melanin.

In a third example, lengths of gray human hair were first soaked in a 0.1 M copper chloride solution. The hair was then rinsed, and immersed in a mixture of 0.01 M dopa (dihydroxyphenylalanine) and 0.1 M beta-alanine. The hair assumed a rich dark color throughout which remained stable and resisted water extraction.

In a fourth example, gray hair was soaked in a 0.1 M copper chloride solution and then rinsed and soaked in a mixture of 0.01 M dopamine and 0.1 M beta-alanine. Once again, the hair assumed a rich dark color throughout.

In other experiments, varying amounts of tyrosine derivatives having a side chain free for indole formation and derivatives having a substituted amine group, i.e. not free for indole formation, were mixed and reacted with beta-alanine or other aliphatic compounds containing an omega-reactive nitrogen moiety. When applied to hair in the presence of an oxidant, as hereinbefore described, these mixtures were found to yield a proportionally darker blond color. For example, while N-acetyldopamine and beta-alanine produced a blond color in gray hair, and dopamine and beta-alanine produced a black color, a 50% mixture of N-acetyldopamine and dopamine produce an intermediate light brown color when used in the process of the present invention.

Alternatively, the above experiments were repeated as described, but the oxidant was premixed with the tyrosine derivative and the reactive nitrogen compound before application to the hair. This premix application obtained results identical to those heretofore described. It is to be understood that the term oxidant, as used herein, is meant to include cupric ions or other substances which gain electrons in the described reactions; but to exclude harsh bleaching chemicals such as hydrogen peroxide, which are antithetical to and not necessary for the practice of the present invention.

In further experimentation, the composition and process of the present invention were shown to affect the coloration of human skin. In a fifth example, 0.1 M copper chloride, 0.1 M beta-alanine and 0.01 M N-acetyldopamine were mixed and applied to the light skin on the inside of the experimenter's wrist for a period of five minutes. A stable golden brown spot was left when the composition was removed. This golden brown color had the appearance of naturally sun tanned human skin and resisted water extraction.

In a sixth example, 0.1 M copper chloride, 0.1 M beta-alanine and 0.01 M dopamine were mixed and applied to light human skin for five minutes. When the composition was removed, a black spot remained which, as in the first example above, resisted water extraction. The addition of incremental amounts of the dopamine solution to the skin tanning mixture of copper chloride, beta-alanine and N-acetyldopamine yielded proportionally darker natural colors.

Thus, it can be seen that the natural colors of human hair and skin may be produced through the process of the present invention. The composition and process described herein employs non-mutagenic materials and may be safely used. The invention may be embodied in other specific forms without departing from the spirit thereof. The embodiment described herein is therefore to be considered in all respects as illustrative and not restrictive, the scope of the invention being indicated by the appended claims rather than by the foregoing description.

What is claimed is:

1. A composition for coloring hair or skin comprising: (a) an effective amount of a tyrosyl derivative having a side chain free for indolization, (b) an effective amount of an omega-amino acid having an aliphatic structure which includes from about three to about six carbon atoms, and (c) an effective amount of an oxidant for imparting a rich, dark color to hair or skin.

2. A coloring composition for imparting a rich, dark color to hair or skin comprising: (a) an effective amount of a tyrosyl derivative selected from the group consisting of DOPA and dopamine, (b) an effective amount of an omega-amino acid selected from the group consisting of beta-alanine, lysine, gamma-amino-butyric acid, beta-amino-isobutyric acid and beta-aminopropionitrile, and (c) an effective amount of an oxidant for imparting said rich, dark color to said hair or skin.

3. A coloring composition for imparting a rich, dark color to hair or skin comprising, on a ratio basis: (a) about one one-hundredth of a mole of DOPA, (b) about one tenth of a mole of beta-alanine, and (c) about one tenth of a mole of copper chloride.

4. A coloring composition for imparting a rich, dark color to hair or skin comprising, on a ratio basis: (a) about one one-hundredth of a mole of dopamine, (b) about one tenth of a mole of beta-alanine, and (c) about one tenth of a mole of copper chloride.

5. A method for imparting a rich, dark color to hair or skin comprising: (1) admixing an effective amount of a tyrosyl derivative having a side chain free for indolization, an effective amount of an omega-amino acid having an aliphatic structure which includes from about three to about six carbon atoms, and an effective amount of an oxidant to produce an admixture capable of imparting said rich, dark color to said hair or skin; and (2) contacting said hair or skin with an effective amount of said admixture to impart said rich, dark color to said hair or skin.

6. The method of claim 5 wherein: said tyrosyl derivative is selected from the group consisting of DOPA and dopamine, and said omega-amino acid is selected from the group consisting of beta-alanine, lysine, gamma-aminobutyric acid, beta-aminoisobutyric acid and beta-aminopropionitrile.

7. A method for imparting a rich, dark color to hair or skin comprising: (1) admixing, on a ratio basis, about one one-hundredth of a mole of dopamine, about one tenth of a mole of beta-alanine, and about one tenth of a mole of copper chloride to produce an admixture capable of imparting said rich, dark color to said hair or skin; and (2) contacting said hair or skin with an effective amount of said admixture to impart said rich, dark color to said hair or skin.

8. A method for imparting a rich, dark color to hair or skin comprising: (1) admixing, on a ratio basis, about one one-hundredth of a mole of DOPA, about one tenth of a mole of beta-alanine, and about one tenth of a mole of copper chloride to produce an admixture capable of imparting said rich, dark color to said hair or skin; and (2) contacting said hair or skin with an effective amount of said admixture to impart said rich, dark color to said hair or skin.

9. A composition for coloring hair or skin comprising: (a) an effective amount of a first tyrosyl derivative having a side chain not free for indolization, (b) an effective amount of a second tyrosyl derivative having a side chain free for indolization, (c) an effective amount of an omega-amino acid having an aliphatic structure which includes from about three to about six carbon atoms, and (d) an effective amount of an oxidant for imparting proportionally darker color to hair or skin relative to a natural color.

10. A coloring composition for imparting proportionately darker color to hair or skin relative to a natural color, comprising: (a) an effective amount of a first tyrosyl derivative selected from the group consisting of N-acetyldopamine and leucyl-tyrosine, (b) an effective amount of a second tyrosyl derivative selected from the group consisting of DOPA and dopamine, (c) an effective amount of an omega-amino acid selected from the group consisting of beta-alanine, lysine, gamma-aminobutyric acid, beta-aminoisobutyric acid and beta-aminopropionitrile, and (d) an effective amount of an oxidant for imparting said proportionately darker color to hair or skin relative to said natural color.

11. A coloring composition for imparting a proportionately darker color to hair or skin relative to a natural color, comprising, on a ratio basis: (a) about one one-hundredth of a mole of N-acetyldopamine, (b) an effective amount of dopamine, (c) about one tenth of a mole of beta-alanine, and (d) about one tenth of a mole of copper chloride, for imparting said proportionately darker color to hair or skin relative to said natural color.

12. A method for imparting a proportionately darker color to hair or skin relative to a natural color, comprising: (1) admixing an effective amount of a first tyrosyl derivative having a side chain not free for indolization, an effective amount of a second tyrosyl derivative having a side chain free for indolization, an effective amount of an omega-amino acid having an aliphatic structure which includes from about three to about six carbon atoms, and an effective amount of an oxidant to produce an admixture capable of imparting said proportionately darker color to said hair or skin relative to said natural color; and (2) contacting said hair or skin with an effective amount of said admixture to impart said proportionately darker color.

13. The method of claim 12 wherein: said first tyrosyl derivative is selected from the group consisting of N-acetyldopamine and leucyl-tyrosine, said second tyrosyl derivative is selected from the group consisting of DOPA and dopamine, and said omega-amino acid is selected from the group consisting of beta-alanine, lysine, gamma-aminobutyric acid, beta-aminoisobutyric acid and beta-aminopropionitrile.

14. A method for imparting a proportionately darker color to hair or skin relative to a natural color, comprising: (1) admixing, on a ratio basis, about one one-hundredth of a mole of N-acetyldopamine, an effective amount of dopamine, about one tenth of a mole of beta-alanine, and about one tenth of a mole of copper chloride to produce an admixture capable of imparting said proportionately darker color to said hair or skin relative to said natural color; and (2) contacting said hair or skin with an effective amount of said admixture to impart said proportionately darker color.

* * * * *